United States Patent
Branch

[11] Patent Number: 5,607,410
[45] Date of Patent: Mar. 4, 1997

[54] VISION DIRECTED EYE WASH

[76] Inventor: John D. Branch, 6055 Windemere, Riverside, Calif. 92506

[21] Appl. No.: 390,418

[22] Filed: Feb. 17, 1995

Related U.S. Application Data

[63] Continuation of Ser. No. 197,116, Feb. 16, 1994, abandoned, which is a continuation-in-part of Ser. No. 18,377, Feb. 16, 1993, abandoned.

[51] Int. Cl.$^6$ .......................... A61H 33/04; A61M 35/00
[52] U.S. Cl. .......................... 604/302; 604/295; 604/300
[58] Field of Search .................... 604/294–302; 128/200.23; 222/498, 527, 533, 556

[56] References Cited

U.S. PATENT DOCUMENTS

| | | | |
|---|---|---|---|
| 2,382,771 | 8/1945 | Bowers | 604/300 |
| 2,736,316 | 2/1956 | Stovall | 604/300 |
| 3,279,466 | 10/1966 | Mings | 604/302 |
| 3,506,001 | 4/1970 | Costello | 604/294 |
| 4,002,168 | 1/1977 | Petterson | 604/298 |
| 4,784,652 | 11/1988 | Wikstrom | 604/295 |
| 4,960,407 | 10/1990 | Cope | 604/300 |
| 5,030,214 | 7/1991 | Spector | 604/295 |
| 5,064,420 | 11/1991 | Clarke et al. | 604/295 |
| 5,178,613 | 1/1993 | Gibilisco | 604/294 |

FOREIGN PATENT DOCUMENTS

| | | | |
|---|---|---|---|
| 1059621 | 6/1959 | Germany | 604/295 |

Primary Examiner—John G. Weiss
Assistant Examiner—K. M. Reichle
Attorney, Agent, or Firm—Harvey S. Hertz

[57] ABSTRACT

A vision directed eye wash system includes an eye support for positioning an eye member to be flushed. A reservoir contains a supply of fluid. A tube is coupled at one end to the reservoir and the other end thereof is positioned adjacent the eye support for dispensing fluid from the reservoir into the eye. A mirror is positioned adjacent the reservoir for enabling the user to view the eye member between flushes. The tube may be positioned in a trough interconnecting the reservoir and eye support. The trough is generally of U-shaped cross-sectional configuration and the axis of the trough and the axis of the reservoir are generally perpendicular to each other when the eye member is viewed in the mirror and parallel to each other when the system is closed for storage.

12 Claims, 4 Drawing Sheets

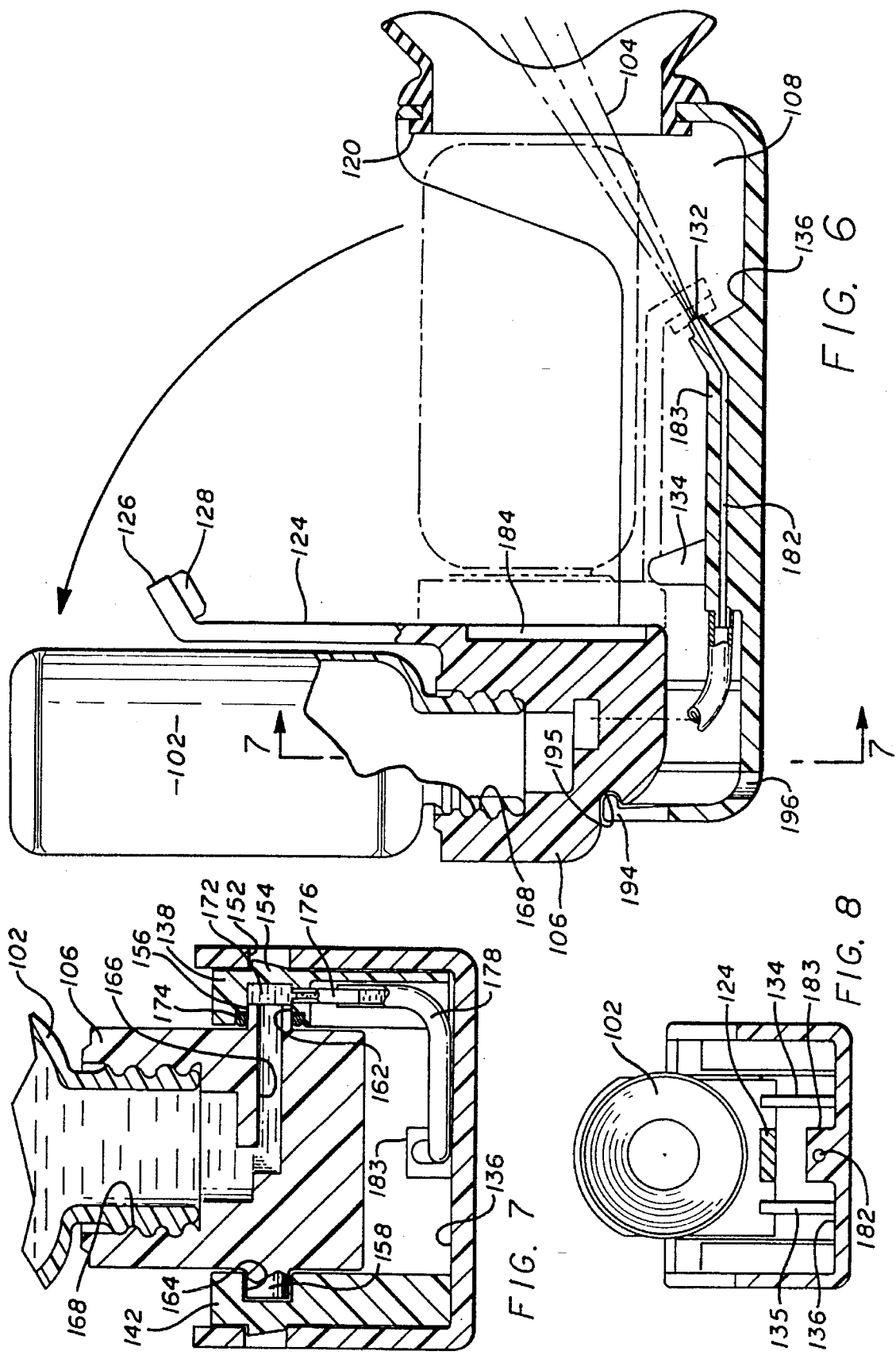

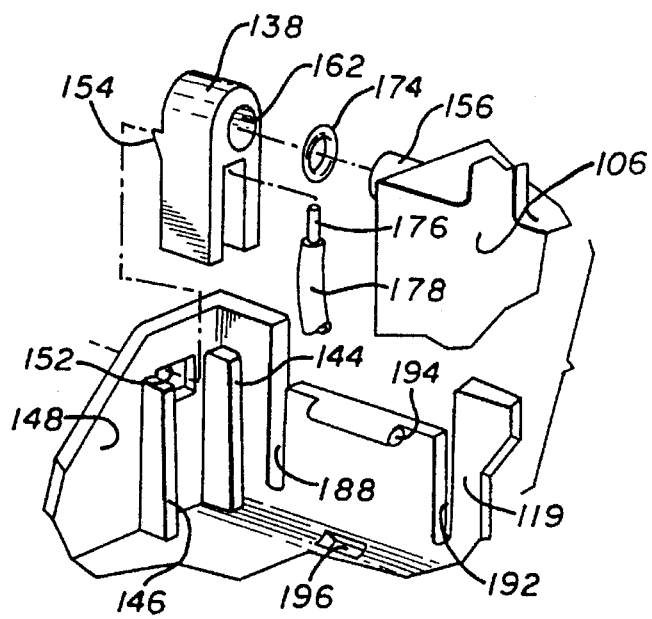
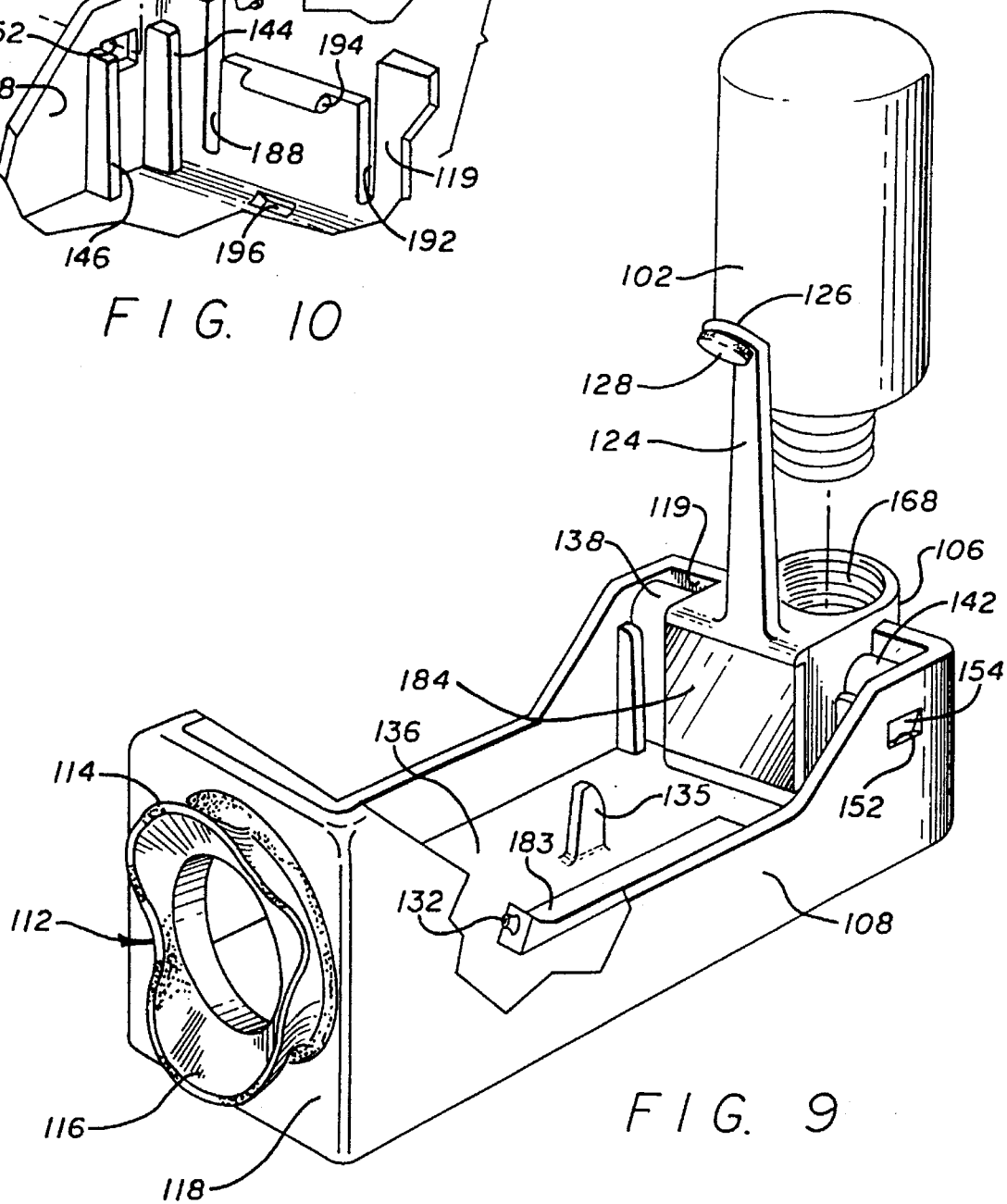
FIG. 10
FIG. 9

VISION DIRECTED EYE WASH

This application is a continuation of application Ser. No. 08/197,116, filed Feb. 16, 1994, which is a continuation-in-part of application Ser. No. 08/018,377, filed Feb. 16, 1993, both now abandoned.

BACKGROUND OF THE INVENTION

1. Field of the Invention

The invention relates in general to an eye wash system for emergency use and, more particularly, to a vision directed portable eye wash.

2. Description of the Prior Art

Prior art emergency eye wash systems have employed sprays of water from regular plumbing as well as portable devices which can be utilized in an emergency where the health and safety of workers are at risk. In such situations the workers are exposed to gases, fumes and liquids, solid materials and other substances which can irritate or injure eyes upon contact therewith. Such devices are well known and typically flood the eyes with a source of liquid such as a saline or sterile water solution. U.S. Pat. No. 4,131,115 contains a combined eyelid turning element, an eye-washing element, a bottle and a mirror for washing an eye. U.S. Pat. Nos. 3,779,245; 2,382,771; and 2,410,257 also utilize mirrors to aid in delivery of a fluid to the eye. Other known prior art includes U.S. Pat. Nos. 2,920,624; 4,012,798; 3,016,898; 4,968,310; 5,030,214; 1,603,727; 4,131,115; 4,002,168; 4,543,096; 3,058,466; 3,439,674; French Patent Nos. 435,542; 692,146 and 457,978; Belgian Patent No. 626,132; and British Patent No. 923,977.

SUMMARY OF THE INVENTION

The present invention provides a portable low-cost eye wash which can be used in an emergency to flush an eye. The eye wash can be used by workers who are exposed to hazardous materials as well as by sportsmen on trips to remote areas. The eye wash contains a saline solution which is directed by the user into the eye, and simultaneously enables the user to examine the eye between sprays. The device enables the eyelid to be kept separate and minimizes blinking during the wash. Further, the eye wash system allows the user to retain the head in a position wherein the eye vision axis is generally horizontal. Operation of the system is immediate once the system is open for operation and the eye is positioned adjacent an eye support. In accordance with the invention, the vision directed eye wash system of the present invention includes an eye support for positioning an eye member to be flushed. A fluid reservoir contains a supply of fluid therein. A tube is coupled at one end to the reservoir and at the other end is positioned adjacent the eye support for dispensing fluid from the reservoir into the eye. A mirror is positioned adjacent the reservoir enabling the eye to be examined between flushes to determine if particles have been flushed from the eye. The tube can be positioned in a trough which interconnects the eye support member and the fluid reservoir and permits fluid run-off away from the user's eye. The trough is generally of a U-shaped cross-sectional configuration and the trough axis and the reservoir axis are generally perpendicular to each other when the eye member is viewed in the mirror. The axes are parallel to each other when the system is closed for storage.

The advantages of this invention, both as to its construction and mode of operation, will be readily appreciated as the same becomes better understood by reference to the following detailed description, when considered in connection with the accompanying drawings, in which like reference numerals designate like parts throughout the figures.

BRIEF DESCRIPTION OF THE DRAWINGS

FIG. 6 is a cross-sectional view of the eye wash of FIG. 4.

FIG. 7 is a cross-sectional view taken along the lines 7—7 of FIG. 6.

FIG. 8 is a cross-sectional view taken along the lines 8—8 of FIG. 5.

FIG. 9 is a front perspective view of the eye-wash of FIG. 4; and

FIG. 10 is a partial exploded view thereof.

DESCRIPTION OF THE PREFERRED EMBODIMENT

Figure 1:
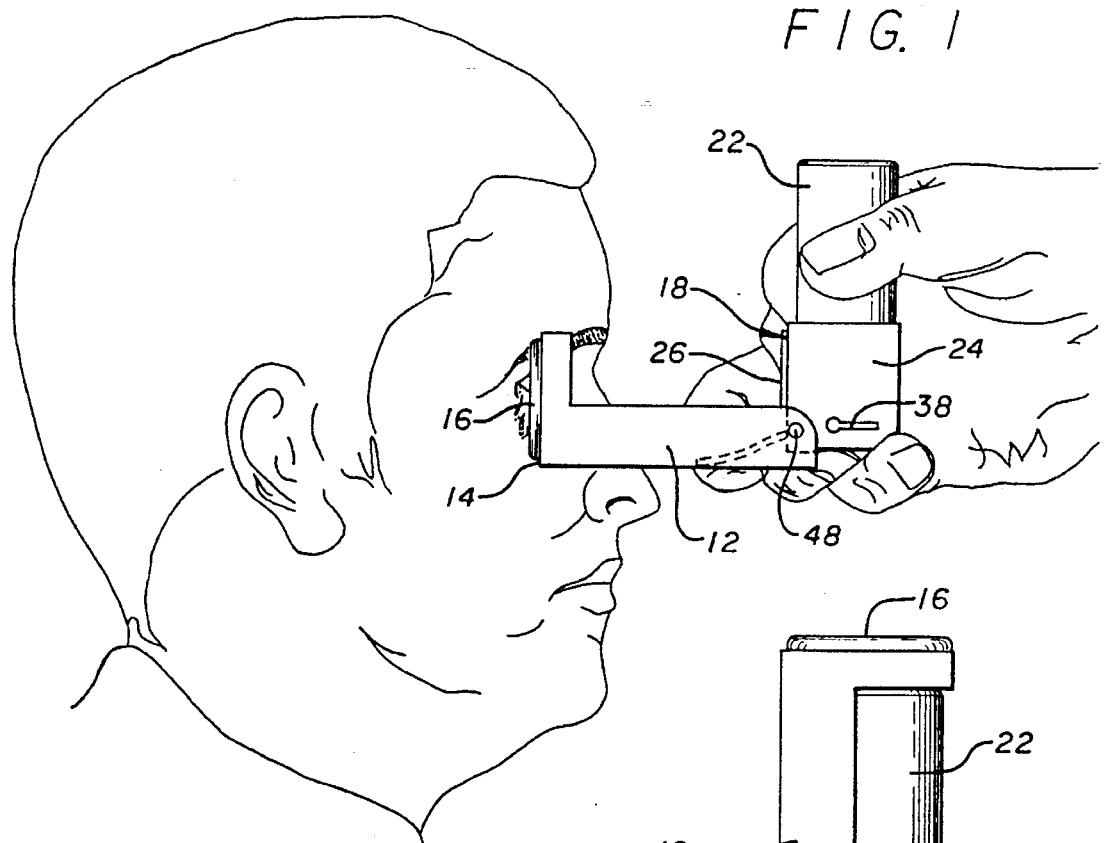
FIG. 1 is a perspective view of the vision directed eye wash in accordance with principles of the invention.

Referring now to the drawings, there is shown in FIG. 1 a vision directed eye wash in an operational position fitted against the eye of a user. A trough 12 contains an end wall 14 having a rubber ring eye piece 16 positioned adjacent the wearer's eye. At the other end of the trough, a reservoir 18 is formed and comprises a plastic squeeze bottle 22 normally containing a saline solution. The squeeze bottle is mounted in a housing 24. A mirror 26 formed in a plane generally parallel to the plane of the rubber eye piece and mounted on the housing 24 enables the user to view his eye between applications of the saline solution to determine if particles have been flushed from the eye.

Figure 2:
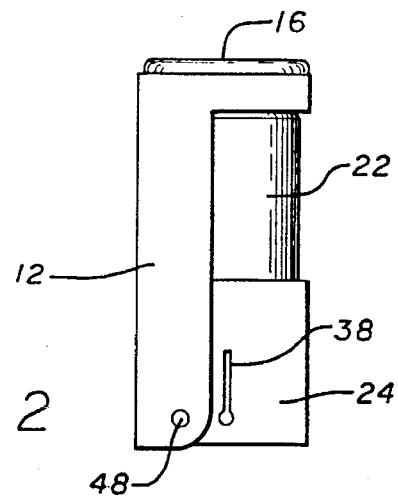
FIG. 2 is a side view of the eye wash of FIG. 1 in a collapsed position.

As can be seen in FIG. 2, in a collapsed position, the trough 12 is pivotally connected to the housing 24 enabling the trough to abut the housing and the bottle 22. Thus, in a closed compact position, the axis of the trough and the axis of the squeeze bottle are generally parallel to each other.

Figure 3:
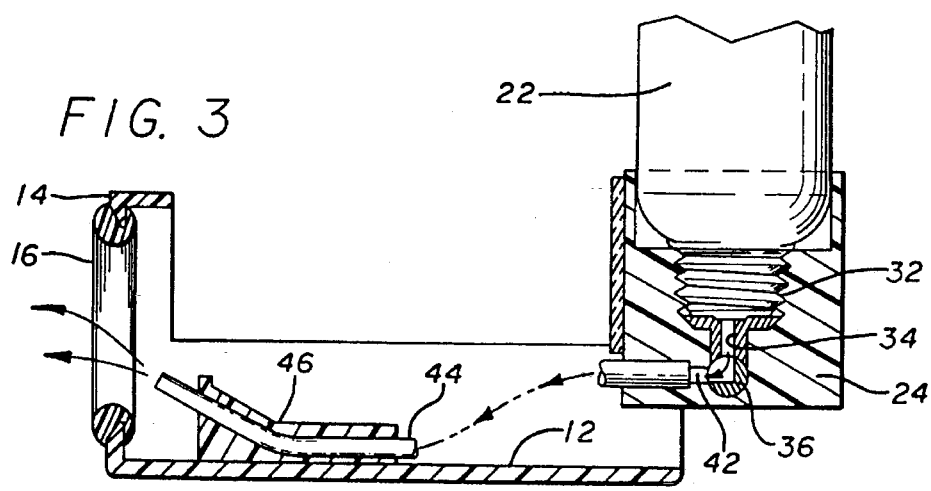
FIG. 3 is a sectional view of the eye wash of FIG. 1.

Referring now to FIG. 3, the eye wash is shown in greater detail. The trough 12 is a generally U-shaped cross-section, and contains the end wall 14 to which the rubber ring eye piece 16 is secured. The opposite end of the trough 12 is open, enabling excess solution to flow away from the user and onto the ground.

The bottle 22 is normally threadably inserted into threads 32 formed in the housing 24. The threaded end of the bottle 22 is coupled to a housing fluid channel 34. A rotatable ball valve 36 which is controlled by a handle 38 on the exterior surface of the housing 24 (FIG. 2) opens the channel 34 to a second channel 42 coupled to one end of a fluid tube 44. The fluid tube 44 is mounted on a fixed support barrel 46 positioned in the trough 12 and a free end of the fluid tube is directed adjacent the rubber ring eye piece 16. Thus, with the ball valve 36 open, squeezing of the plastic bottle 22 as shown in FIG. 1, causes a fluid spray to be applied to the eye of the user when the eye is positioned adjacent the rubber ring 16.

When stored, the eye wash is normally in the position shown in FIG. 2. The user rotates the trough 12 about a 90 degree hinge 48 secured to the housing 24 so that the axis thereof is at right angles of the axis of the squeeze bottle 22 and the rubber ring 16 is positioned adjacent the eye. Then the ball valve 36 is opened by movement of the handle 38 and the bottle 22 squeezed to apply the solution in the bottle to the eye. Water will flow toward the eye from the fluid tube 44.

A rubber eye piece 16 has been found to be preferable to a plastic eye piece as the rubber eye piece provides greater friction to keep the eyelids apart, minimizing blinking during the wash procedure. Normally, the user squeezes the bottle 22 to apply the solution to the eye and between applications, can view the eye in the mirror 26. It should be noted that the support barrel 46 is positioned so that the end of the fluid tube 44 aims the solution directly at the eye in the center of the ring 16.

Figure 4:
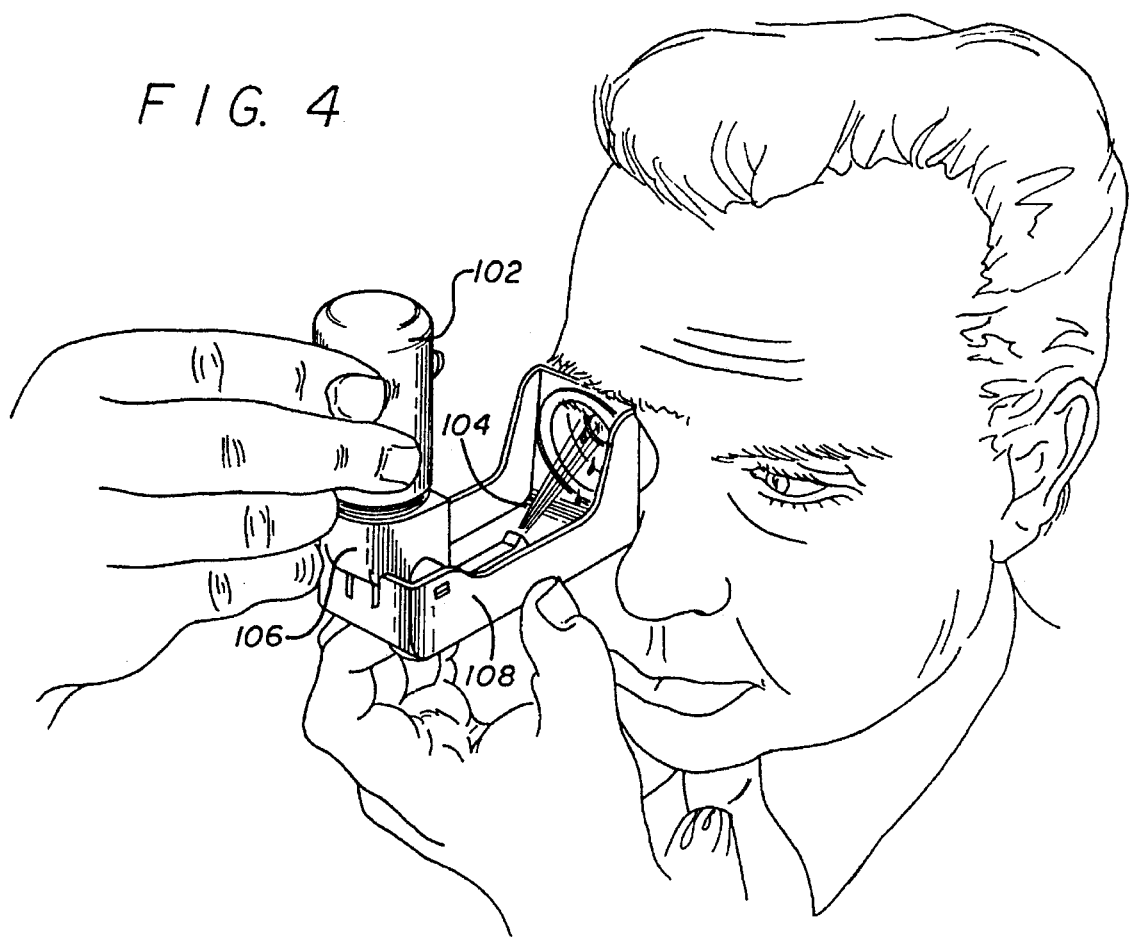
FIG. 4 is a perspective view of an alternate arrangement of the vision directed eye wash.
Figure 5:
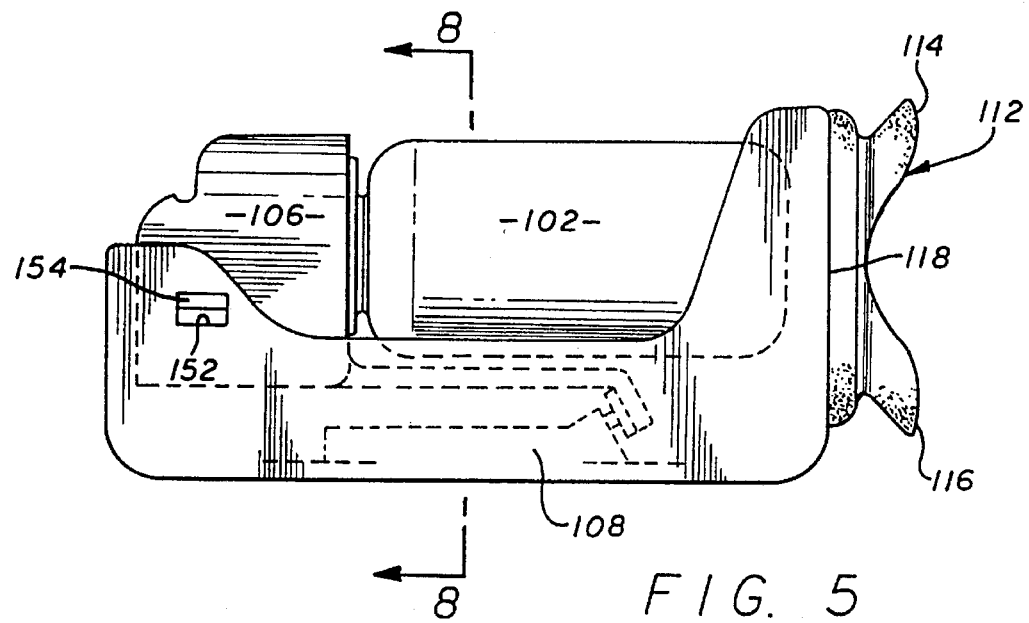
FIG. 5 is a side view of the eye wash of FIG. 4 in a collapsed position.

Referring now to FIGS. 4 through 10, there is shown an alternate arrangement of the eye wash embodiment of FIGS. 1 through 3. The eye wash of FIGS. 4 through 10 are similar to that of FIGS. 1 through 3 in that a plastic squeeze bottle 102 illustrated in FIG. 4 is also utilized to direct a flow of fluid 104 into a user's eye. The squeeze bottle 102 is mounted on a housing 106 and as shown in FIG. 5, the squeeze bottle and the housing can be rotated in a 90 degree angle so that it folds into a trough 108 when not in use.

A rubber eye piece 112 has been modified from the version shown in FIGS. 1 through 3 and, of course, could be substituted into the embodiment of FIG. 1 through 3. The eye piece 112 contains upper and lower flared flanges 114 and 116, respectively, which forces the upper and lower lids of the eye apart when the eye wash is used. The eye piece 112 can be shown in frontal perspective view in greater detail in FIG. 9.

FIG. 9 further illustrates the trough 108 in greater detail. The trough 108 is generally U-shaped along its longitudinal axis and contains a front end wall 118 which has a central aperture for enabling the mounting ring 120 of eye piece to be inserted. The rear end wall 119 of the trough 108 has an upper central section partially removed, as will be explained in greater detail hereinafter, enabling the housing 106 to rotate from the inoperative position to an operative position as shown by the arrow in FIG. 6.

A stop post 124 extends from the top wall of the housing 106 in front of the squeeze bottle 102. The stop post top free end 126 is angled inwardly toward the center of the trough and contains a cushion 128 thereon. The cushion 128 which is typically made of rubber or other flexible material, covers the spray outlet 132 when the housing 106 is rotated to the inoperative position of FIG. 5, thus eliminating the need for a shut-off valve when the device is not in use. In addition, a pair of posts 134 and 135 extend upwardly from the bottom wall 136 of the trough 108 and form a stop abutting a portion of the housing 106 when it is pivoted to the horizontal position as shown in dashed lines in FIG. 6. The posts 134 and 135 can be seen in FIG. 8, while only post 134 and post 135 can be seen in FIG. 6 and FIG. 9, respectively.

Referring now to FIGS. 7 and 10, the mounting of the housing 106 in the trough 108 is shown in greater detail. The housing 106 is rotatably positioned on a pair of locator blocks 138 and 142. As shown in FIG. 10, the locator block 138 is positioned between a pair of supports 144 and 146, integrally formed on the side wall 148 of the trough. A locking hole 152 in the side wall 148 intermediate the supports 144 and 146 enable a locking tab 154 formed in the locator block 138 to be inserted therein. The locator block 142 is similarly positioned on the other side of the trough 108.

The housing 106 further contains a pair of integrally formed cylindrical sleeves 156 and 158 which enable the body 106 to rotate from the open to closed position as shown in FIG. 6. The sleeves fit in recesses 162 and 164 formed in the locator blocks 138 and 142, respectively, and can rotate therein.

The flow of fluid from the bottle 102 to the outlet spray 132 is defined by a path including a channel 166 which is connected to the threaded inlet 168 of the housing 106. The channel 166, in turn, is formed in the cylindrical sleeve 156 with the channel outlet connected to a space 172 formed between the end of the cylindrical sleeve 156 and the interior of the locator block 138. An O-ring 174 surrounds the cylindrical sleeve 156 and prevents leakage therefrom.

A metal tube 176 interconnects the space 172 in the locator block 138 to a rubber tube 178 which in turn is interconnected to a channel 182 integrally formed in a raised ridge section 183 in the bottom wall 136 of the trough 108. The other end of the channel 182 is coupled to the spray outlet 132 of the spray nozzle.

As shown in FIG. 9, a mirror 184 is mounted on the housing 106 so that when the user's eye is placed in the eye piece 112, the viewing axis of the eye, when in a horizontal position, is perpendicular to the plane of the mirror. In addition, the spray outlet 132 is positioned so that the direction of spray is at an acute angle with respect to the horizontal viewing axis. Thus, once again, when the bottle 102 is squeezed the spray from the spray outlet 132 will be directed toward the user's eye. After spraying the user can examine his eye by directing his vision toward the mirror 184.

It should be noted that the housing 106 is mounted on the rear wall of the trough with a pair of vertical grooves 188, 192 formed therein so that an inwardly extending section 194 intermediate the grooves abuts a horizontal groove 195 in the housing 106 (FIG. 6). The trough rear wall section intermediate the vertical grooves 188, 192 thus acts like a spring clip or live hinge.

A drain hole 196 in the trough bottom wall below the housing 106 forms an over flow for excess fluid and permits fluid run-off away from the user.

Thus, as can be readily seen, the arrangement of FIGS. 4–10 enables a user to rotate the bottle 102 and housing 106 to the position shown in FIG. 4, place the eye member adjacent the eye support 112 and squeeze the plastic bottle spraying the injured eye member with a solution almost immediately. The user need not tilt the user's head or aim the spray in a direction. Immediately thereafter the user can then examine the eye and reapply the solution if needed.

I claim:

1. A vision directed eye wash system comprising:

an eye support for positioning an eye member to be flushed thereon;

a fluid reservoir formed of a container having an axis and containing a supply of fluid therein;

a tube coupled at one end to said reservoir and another end thereof positioned adjacent the eye support for dispensing said fluid in said reservoir into the eye;

a mirror positioned adjacent said reservoir for enabling a user to observe the eye between flushes, said eye support and said mirror being formed in generally parallel planes for enabling the user to view his eye between applications of said fluid; and a trough interconnecting said fluid reservoir and said eye support, said trough having a longitudinally extending axis and side walls interconnected by a bottom wall to collect excess solution flowing from said tube when fluid is dispensed and to direct fluid away from the eye support, said tube including a portion adjacent said another end positioned in said trough and extending along and mounted directly on said bottom wall of said trough.

2. A vision directed eye wash system in accordance with claim 1, wherein said trough is generally U-shaped in cross-section, the axis of said trough being formed perpendicular to said U-shaped trough cross-section, said trough axis and said reservoir axis being generally perpendicular to each other when the eye member is viewed in said mirror, and said axes are parallel to each other when said system is closed for storage.

3. A vision directed eye wash system in accordance with claim 2 wherein said eye support is formed of a rubber ring mounted on an end wall of said trough for minimizing blinking when dispensing said fluid, and an eye vision axis is adapted to be parallel to the axis of said trough member when said eye vision axis is adapted to be perpendicular to the plane of said mirror and said eye support.

4. A vision directed eye wash system in accordance with claim 3 wherein said eye support contains upper and lower flared flanges which are adapted to abut upper and lower eyelids, respectively, when the eye member is placed adjacent said eye support forcing the eyelids apart.

5. A vision directed eye wash system in accordance with claim 1 wherein said another end of said tube is raised above the said trough bottom wall.

6. A vision directed eye wash system comprising:

a friction ring eye support for positioning an eye member to be flushed thereon, said eye member having an eye vision axis;

a fluid reservoir formed of a container containing a supply of fluid therein, said reservoir being mounted in a housing;

a trough adapted to have the eye member positioned at one end thereof and having said reservoir at another end thereof, said trough being formed of side walls interconnected by a bottom wall;

fluid path means for interconnecting said reservoir to a fluid path outlet, said fluid path means including a fluid path portion formed within said trough, mounted directly to and along said bottom wall;

a mirror mounted on said housing in a plane parallel to the plane of said eye support; and said outlet being positioned adjacent the end of said trough where the eye member is positioned for directing fluid toward said eye support at an angle to an axis perpendicular to the plane of said mirror and said eye support and adapted to enable retention of a user's head in a position where the eye vision axis is generally horizontal.

7. A vision directed eye wash system in accordance with claim 6 wherein said fluid path outlet is raised above said trough bottom wall.

8. Apparatus in accordance with claim 6, wherein said housing is pivotally mounted on said another end of said trough.

9. A vision directed eye wash system comprising:

an eye support for positioning an eye member to be flushed thereon;

a fluid reservoir formed of a container containing a supply of fluid therein, said reservoir being mounted in a housing;

a trough adapted to have the eye member positioned at one end thereof and having said reservoir at the other end thereof, said trough having a fluid path formed therein for interconnecting said reservoir to an outlet adjacent said eye support;

a mirror mounted on said housing in a plane parallel to the plane of said eye support;

said outlet being positioned for directing fluid toward said eye support at an angle to an axis perpendicular to the plane of said mirror and said eye support; and said housing and said reservoir being joined together rotate into said trough when not in use, said housing containing a cushion for covering said outlet when said housing and reservoir are rotated into said trough for shutting off the flow of fluid from said outlet.

10. A vision directed eye wash system comprising:

an eye support for positioning an eye member to be flushed thereon;

a fluid reservoir formed of a container containing a supply of fluid therein, said reservoir being mounted in a housing;

a trough adapted to have the eye member positioned at one end thereof and having said reservoir at the other end thereof, said trough having a fluid path formed therein for interconnecting said reservoir to an outlet adjacent said eye support;

a mirror mounted on said housing in a plane parallel to the plane of said eye support;

said outlet being positioned for directing fluid toward said eye support at an angle to an axis perpendicular to the plane of said mirror and said eye support; and said housing and said reservoir being joined together to rotate into said trough when not in use, said housing containing a means for covering said outlet when said housing and reservoir are rotated into said trough for shutting off the flow of fluid from said outlet.

11. A vision directed eye wash system comprising:

an eye support for positioning an eye member to be flushed thereon;

a housing;

a fluid reservoir positioned in said housing and formed of a container having an axis and having a supply of fluid therein;

a tube coupled at one end to said reservoir and another end thereof positioned for dispensing fluid in said reservoir into the eye member;

a rotatable sleeve formed in said housing enabling said housing to rotate; and means for coupling said one end of said tube to said reservoir, said means comprising a fluid channel extending axially through said rotatable sleeve.

12. Apparatus in accordance with claim 11 wherein said housing and said reservoir are joined together to rotate to a position for shutting off the flow of fluid from said reservoir.

* * * * *